United States Patent [19]
Goulding et al.

[11] Patent Number: 5,750,051
[45] Date of Patent: May 12, 1998

[54] REACTIVE TERPHENYLS

[75] Inventors: Mark Goulding; David Coates; Simon Greenfield, all of Dorset, Great Britain

[73] Assignee: Merck Patent Gesellschaft Mit Beschrankter Haftung, Darmstadt, Germany

[21] Appl. No.: 623,163

[22] Filed: Mar. 28, 1996

[30] Foreign Application Priority Data

Mar. 29, 1995 [EP] European Pat. Off. .............. 95104633

[51] Int. Cl.$^6$ .................... C09K 19/12; C09K 19/52; C08F 22/00
[52] U.S. Cl. ................... 252/299.65; 252/299.01; 252/299.66; 252/299.64; 252/299.67; 349/183; 349/184; 349/186; 526/318.1; 526/319; 428/1
[58] Field of Search ............... 252/299.1, 299.66, 252/299.65; 349/183, 184, 186; 526/318.1, 319; 428/1

[56] References Cited

U.S. PATENT DOCUMENTS 5,354,498 10/1994 Akashi et al. ............... 252/299.01
5,516,455 5/1996 Jacobines et al. ............. 282/299.01
5,560,864 10/1996 Goulding .................... 252/299.01

*Primary Examiner*—Shean C. Wu
*Attorney, Agent, or Firm*—Millen, White, Zelano & Branigan, P.C.

[57] ABSTRACT

The invention relates to monofunctional reactive terphenyls of formula I

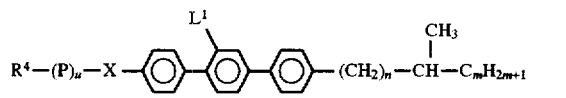

in which
$R^4$ is $CH_2=CW-COO-$,

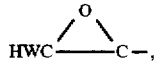

$HWN-$, $CH_2=CH-$, $CH_2=CH-O-$ or $HS-CH_2-(CH_2)_m-COO-$ with W being H, Cl or alkyl with 1–5 C atoms and m being 1–7,
P is alkylene with up to 12 C atoms, it being also possible for one or more non adjacent $CH_2$ groups to be replaced by $-O-$,
$L^1$ is H or F,
X is $-O-$, $-S-$, $-COO-$, $-OCO-$ or a single bond,
u is 0 or 1,
n is an integer 1 to 8, and
m is an integer 2 to 8.

9 Claims, No Drawings

REACTIVE TERPHENYLS

FIELD OF THE INVENTION

The invention relates to monofunctional reactive terphenyls of formula I

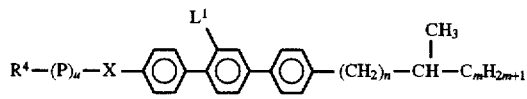

in which
$R^4$ is $CH_2=CW-COO-$,

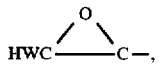

$HWN-$, $CH_2=CH-$, $CH_2=CH-O-$ or $HS-CH_2$ $(CH_2)_m-COO-$ with W being H, Cl or alkyl with 1-5 C atoms and m being 1-7,
P is alkylene with up to 12 C atoms, it being also possible for one or more non adjacent $CH_2$ groups to be replaced by $-O-$,
$L^1$ is H or F,
X is $-O-$, $-S-$, $-COO-$, $-OCO-$ or a single bond,
u is 0 or 1,
n is an integer 1 to 8, and
m is an integer 2 to 8.

Furthermore, the invention relates to a liquid crystalline material in the form of an anisotropic film or gel comprising a polymerized monotropic or enantiotropic liquid crystalline material and a low-molecular weight liquid crystalline material, wherein the polymerized material a) forms a permanently oriented network in the low-molecular weight liquid crystalline material b), characterized in that the polymerized material a) is obtainable by (co)-polymerization of a chiral polymerizable terphenyl of formula I.

BACKGROUND OF THE INVENTION

EP 0 606 940 discloses a broad band cholesteric polarizer obtainable by co-polymerization of a chiral reactive and a non-chiral reactive mesogenic compound. There is a demand for chiral reactive compounds which yield chiral smectic or chiral nematic polarizer with a broader band of the helical pitch. This problem can be solved with the aid of the novel terphenyls of formula I.

L. K. M. Chan et al., Mol. Cryst. Liq. Cryst. 158 B, 209 (1988), disclose chiral low molecular weight terphenyls of formula

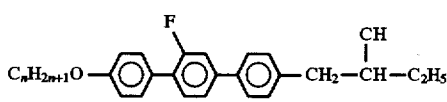

There is no hint to polymerizable compounds of this type.

SUMMARY OF THE INVENTION

Preferred embodiments of the invention are:
a) Monofunctional reactive terphenyl of formula I in which n is 1, and
m is 2.

b) Copolymerizable precursor material comprising at least one polymerizable terphenyl of formula I and at least one bifunctional reactive achiral compound of formula II

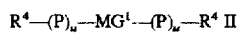

wherein $R^4$, P and u have the meaning given, and
$MG^1$ is a mesogenic group, in particular in which
$R^4$ is an acrylate radical of formula

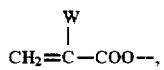

wherein W has the meaning given, or in which $R^4$ is a vinylether radical of formula $CH_2=CH-O-$.

c) Copolymerizable material comprising formula II in which $MG^1$ is selected from

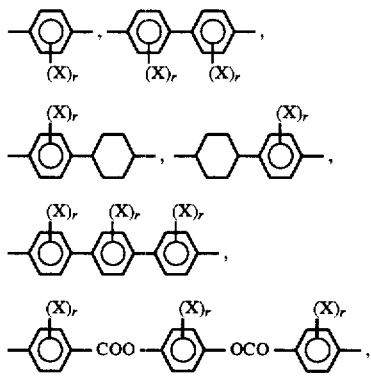

with X being CN or F and r being 0, 1 or 2.

Another aspect of the invention is a chiral smectic or nematic polymer film obtainable by in-situ (co) polymerization of a polymerizable terphenyl of formula I or a copolymerizable material comprising such a terphenyl, in particular a polymer film being capable of selectively reflecting light of visible wavelengths. Furthermore, the invention relates to the use of such a polymer film is as a broad-band polarizer.

Another aspect of the present invention is a chiral smectic C film obtainable by the steps comprising
a) ordering the copolymerizable precursor material or compound of formula I in the monomeric state in the presence of an UV initiator and optionally an additive, and
b) in situ UV polymerization of the resulting ordered precursor material.

Preferred compounds of formula I are those of formulae I1 to I10:

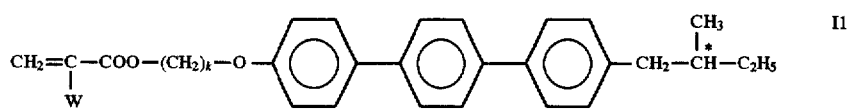

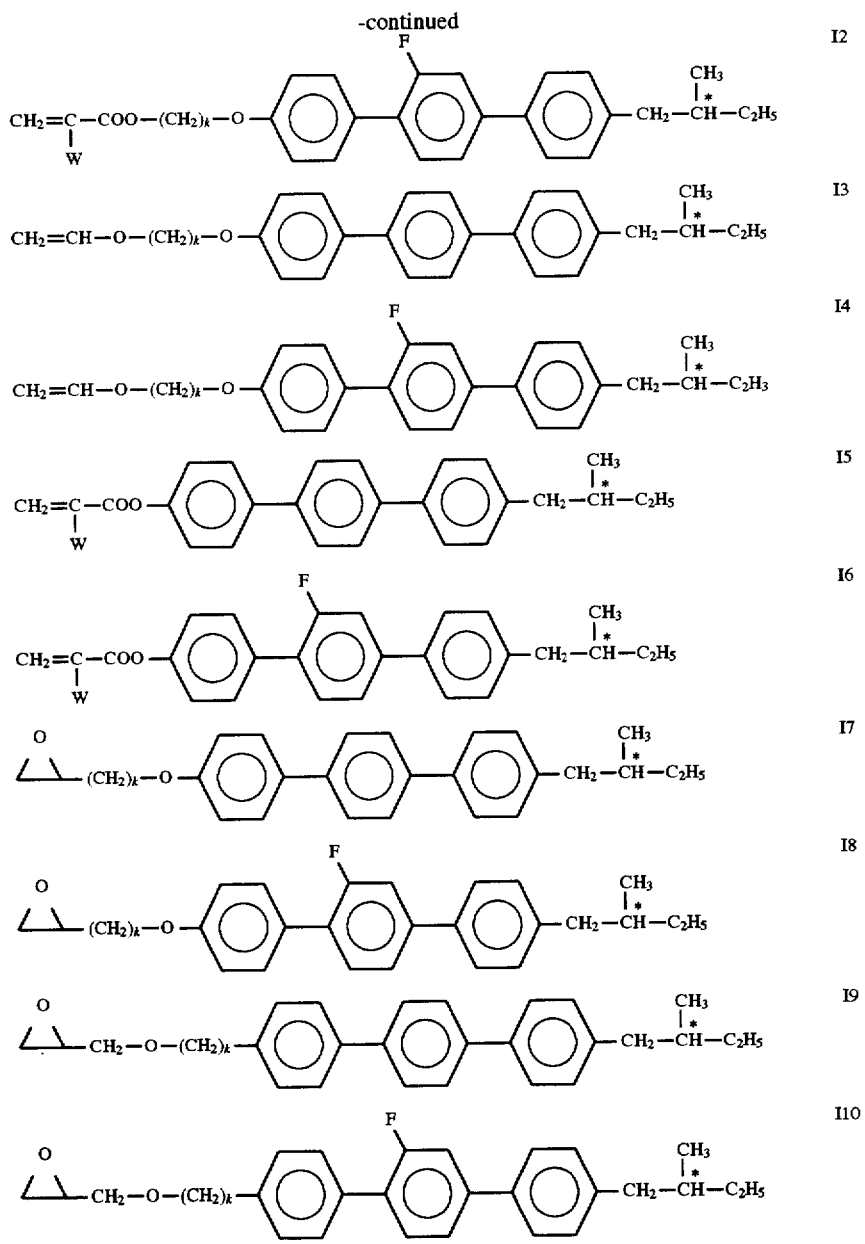

in which W has the meaning given, k is an integer between 2 and 10.

In the compounds of formulae I, I1 to I10 $R^4$ is $CH_2=CW-COO-$, $CH_2=CH-O-$,

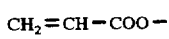

$HWN-$, $HS-CH_2-(CH_2)_m-COO-$ with W being H, Cl or alkyl with 1-5 C atoms and m being 1-7.

Preferably, $R^4$ is a vinyl ether group, an acrylate group, an amino group or a mercapto group, and especially preferred are the following meanings of $R^4$:

$CH_2=CH-COO-$     $R^4$-1

$CH_2=C-COO-$     $R^4$-2
  |
  $CH_3$ $CH_2=C-COO-$     $R^4$-3
  |
  Cl $CH_2=CH-O-$     $R^4$-4

$H_2N-$     $R^4$-5

$H(alkyl)N-$     $R^4$-6

$HS-CH_2-(CH_2)_m-COO-$     $R^4$-7

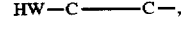     $R^4$-8 with alkyl denoting $C_1$–$C_3$-alkyl and m being 1-5.

In the compounds of formulae I, I1 to I9, the spacer-type group P is alkylene with up to 24 C atoms, it is also being possible for one or more non adjacent $CH_2$ groups to be replaced by O.

In case P is alkylene, P may be straight-chain or branched. P especially preferred is ethylene, propylene, butylene, 1-methyl-propylene, 2-methyl-propylene, pentylene, 1-methyl-butylene, 2-methyl-butylene, hexylene, 2-ethyl-butylene, 1,3-dimethyl-butylene, hephylene, 1-methylhexylene, 2methylhexylene, 3-methylhexylene, 4-methylhexylene, 5-methylhexylene, 6-methylhexylene, octylene, 3-ethyl-hexylene, nonylene, 1-methyl-octylene, 2-methyloctylene, 7-methyloctylene, decylene, undecylene, dodecylene, 2-methylundecylene, 2,7,5-trimethyl-nonylene or 3-propyl-nonylene.

In case P is mono- or polyoxaalkylene, P may be straight-chain or branched. In particular, P is 1-oxa-ethylene, 1-oxa-propylene, 2-oxapropylene, 1-oxa-butylene, 2-oxabutylene, 1,3-dioxabutylene, 1-oxa-pentylene, 2-oxa-pentylene, 3-oxy-pentylene, 2-oxa-3-methyl-butylene, 1-oxahexylene, 2-oxa-hexylene, 3-oxa-hexylene, 1,3dioxa-hexylene, 1,4-dioxy-hexylene, 1,5-dioxa-hexylene, 1-oxy-heptylene, 2-oxa-heptylene, 1,3-dioxa-heptylene, 1,4-dioxa-heptylene, 1,5-dioxa-heptylene, 1,6-dioxa-heptylene, 1,3,5-trioxa-heptylene, 1-oxaoctylene, 2-oxa-octylene, 3-oxa-octylene, 4-oxa-octylene, 1,3-dioxa-octylene, 1,4-dioxa-nonylene, 1,4-dioxa-decylene, 1,3-dioxa-undecylene, 1,4dioxa-undecylene and 1,3,5-trioxa-dodecylene.

X is —O—, —S—, —COO—, —OCO— or a single bond and in particular —O—, —COO—, —OCC— or a single bond. In case X is —O—, —S— or —OCO—, the adjacent $CH_2$— group of Q is not replaced by —O—.

Preferred chiral radicals

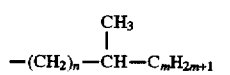

are each independently, 2-methylbutyl, 2-methylpentyl, 3-methylpentyl, 2-ethylhexyl, 2-propyl-pentyl, in particular 2-methylbutyl, 4-methylhexyl,.

The inventive terphenyls can be prepared for example according to the following schemes:

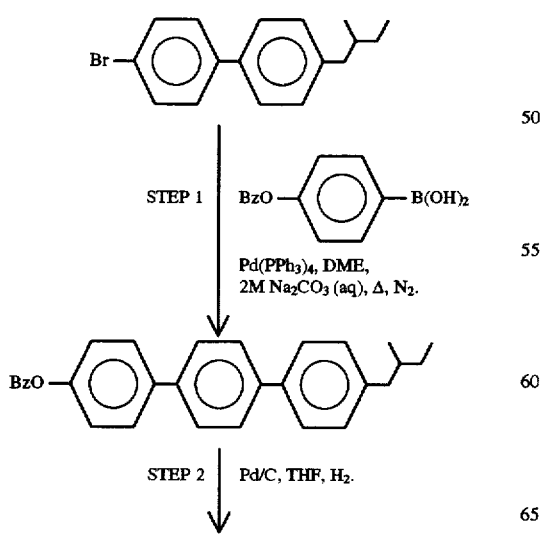

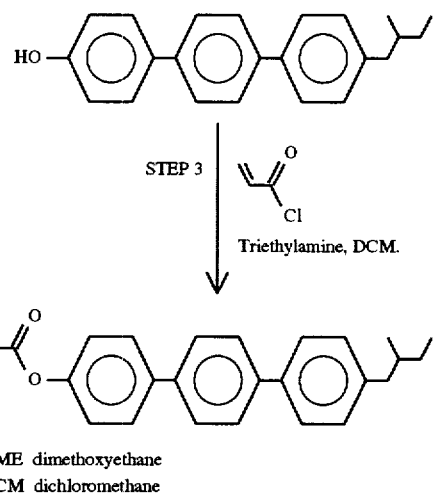

DME dimethoxyethane
DCM dichloromethane

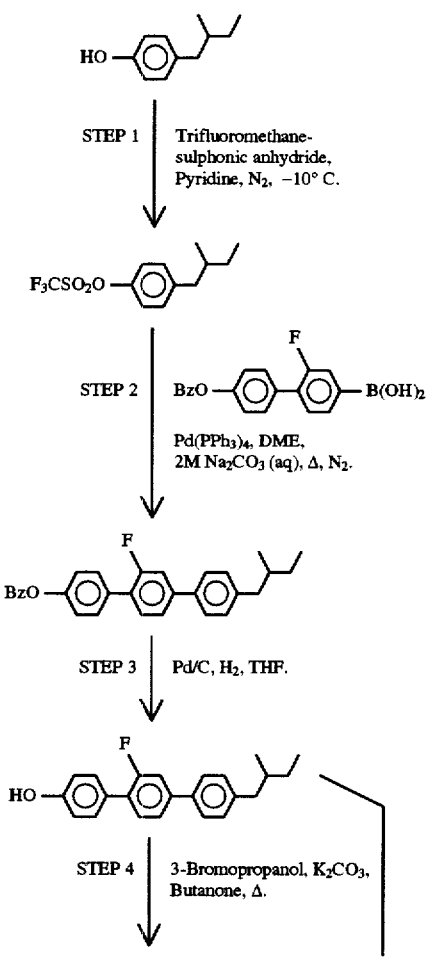

-continued
Scheme 2

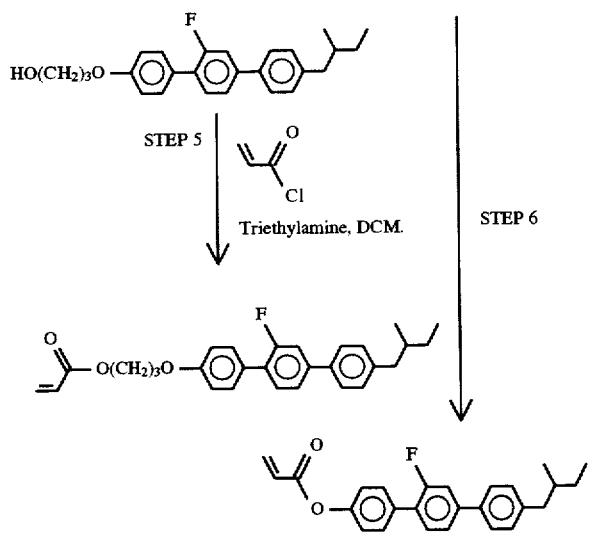

Scheme 3

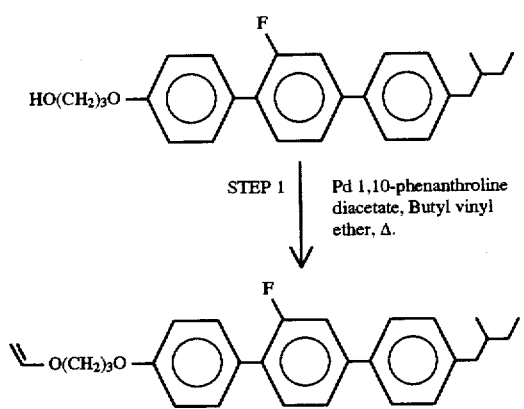

Scheme 4

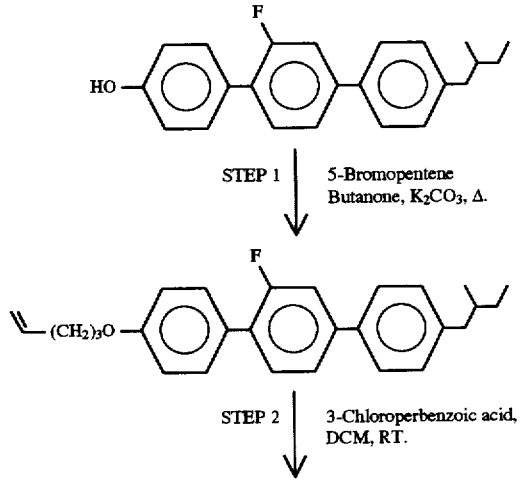

-continued
Scheme 4

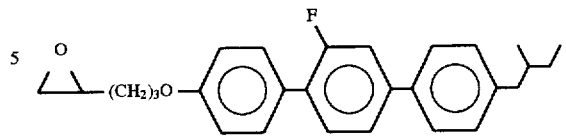

The inventive display exhibits two opposite plates which are transparent to light and which will hereinafter be termed substrates and which comprise electrodes on the opposing sides, said electrodes being manufactured from, for example, $In_2O_3$, $SnO_2$. On the electrode there is provided an orientation layer of, for example, rubbed polyimide or polyamide by means of which the liquid crystalline material according to the invention can be homogeneously aligned between the electrodes. The cell is manufactured by arranging the substrates thus formed and provided with electrodes closing the apertures by, for example, a ring-shaped member and filling the space between the substrates and the ring with the liquid crystalline material according to the invention. In practice, a bonding layer of an epoxy compound can be used instead of the ring shown.

The liquid crystalline material can be capillary filled between two substrates which are provided with electrode layers, and is then subsequently cured, for example, by irradiation with UV light, preferably in the presence of a photoinitiator, for example, an Irgacure® or a Degacure®. Another possible but less attractive technique comprises coating of the LC material on a substrate with subsequent curing. The film may be peeled off and arranged between 2 substrates provided with electrode layers. It is also possible that the substrate onto which the LC material is applied exhibits an electrode layer so that the electrooptical system can be obtained by applying a second electrode layer and, optionally, a second substrate onto the coated and cured film.

The electrooptical system according to the invention can be operated reflectively or transmissively so that at least one electrode and, if present, the associated substrate are transparent. Both systems customarily contain no polarizers, as a result of which a distinctly higher light transmission results and is a considerable technological simplification in the production of these systems compared with conventional liquid crystal systems such as, for example, TN or STN cells.

In general a nematic liquid crystal of positive dielectric anisotropy is desirable because these mixtures would be used in devices in which it is essential to electrically switch a thin film of such a mixture into a homeotropic alignment (field on state) and therefore appear clear to transparent, while the off state would usually be determined by the alignment within the cell, which is usually homogenous and this would give either focal conic (slightly scattering) or grandjean (coloured). It is possible that depending on how the voltage is applied or removed one can flip into either the coloured grandjean or the slightly scattering focal conic state in the field off state. Moreover by adding a small amount of a liquid crystal each state can be stabilized to give a bistable device with one stage being colored (grandjean texture) or essentially clear or slightly light scattering (focal conic). When placed against a black background a contrast between colored and black is clearly seen. The color being dependent on the pitch length of the cholesteric helix according to the equation $$\lambda_{max} = \bar{n} P \sin \Theta$$

$\bar{n}$=mean refractive index of the LC, P=pitch length

Θ=viewing angle

The pitch length obtained when adding a chiral dopant to a nematic host depends on the polarising ability of the LC molecules—the more polarizable they are the tighter the pitch length obtained (higher twisting power), so using a non-polar host may significantly alter how much chiral dopant would be needed to produce a given colour.

Another application for this "blend" of chiral components is to mix them with reactive liquid crystals (for example of formula II) and produce a chiral colored reactive LC mixture which can be coated into a thin film and polymerised by UV light to give a thin polymer film which is colored. It would contain 20–80% reactive chiral LC as above, therefore the reactive non-chiral LC content is 80–20%.

The rise time increases as the cell thickness increases, but the decay time remains constant. The decay time decreases rapidly as the content of network molecules increases. Consequently, it is not the thickness of the cell that counts but the average distance between the network molecules. This explains the short decay times in comparison with the decay times (a few hundred milliseconds) in normal nematic cells. More particularly, decay times of a few milliseconds can be obtained.

The novel chiral reactive liquid crystalline compounds and compositions are highly suitable to produce cholesteric films which can be used in different optical and electrooptical applications.

Furthermore, they are useful as colored films for decorative applications. Since some of them show thermochromism, they can be used as temperature indicators, in particular as reversible or irreversible temperature indicators depending on their grade of polymerizations.

The invention will be explained in more detail by means of the following examples of the preparation of a liquid crystalline material according to the invention.

The mesogenic phases are abbreviated as following:

| K | crystalline |
|---|---|
| N | nematic |
| S | smectic |
| BP | blue phase |
| N* | chiral nematic (cholesteric) |
| HTP | helical twisting power |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application EP 95104633.3, are hereby incorporated by reference.

EXAMPLE 1

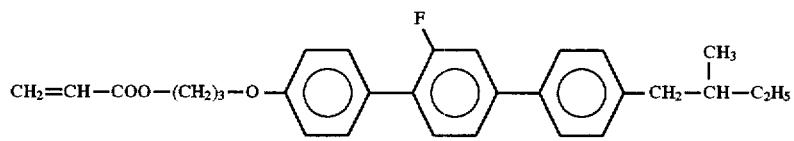

a) The preparation of (S)-(+)-2'-fluoro-4-(3-hydroxypropoxy)4"-(2methylbutyl)-1,1':4',1"-terphenyl was performed according reaction scheme 2, STEP 4 using (S)—(+)-2'-fluoro4-hydroxy-4"-(2-methylbutyl)-1,1':4',1"-terphenyl; 5.6 g (96% yield), 95% pure by HPLC. MS: m/z 394, 393, 392(M??), 391, 337, 336, 335, 334, 333, 279, 278, 277, 276, 249, 248, 233, 220, 207, 184, 170, 139, 138, 115, 91, 77, 59, 57, 41, 32, 29, 27.

b) Preparation of (S)-(+)4-(3-acryloyloxypropoxy)-2'-fluoro4"-(2methylbutyl)-1,1':4',1"-terphenyl was performed according reaction scheme 2, STEP 5 using (S)—(+)-2'-fluoro-4-(3-hydroxypropxy)4"-(2-methylbutyl)-1,1':4',1"-terphenyl; 1.6 g (65% yield), 99% pure by HPLC, C 65.5 ($S_c^*$50.1) N*104.0 BP 104.5 I, HTP=4.831 μm$^{-1}$. MS: m/z 448, 447, 446(M+), 389, 335, 333, 317, 278, 277, 276, 249, 248, 233 220, 183, 139, 115, 114, 113, 85, 73, 58, 57, 55, 41, 29.

EXAMPLE 2

(S)—(+)-2'-Fluoro4"-(2-methylbutyl)-4-(pent-5-enyloxy)-1,1':4',1"-terphenyl

Preparation of (S)-(+)-2'-Fluoro4"-(2-methylbutyl)-4-(pent-5-enyloxy)-1,1':4',1"-terphenyl was performed according reaction scheme 4, STEP 1 using (S)—(+)-2'-fluoro4-hydroxy4"-(2-methylbutyl)-1,1':4',1"-terphenyl and 5-bromopent-1-ene; 1.2 g (86% yield), 93% pure by HPCL.

MS: m/z 404, 403, 402(M+), 373, 347, 346, 345, 334, 333, 303, 279, 278, 277, 276, 249, 248, 233, 220, 202, 183, 157, 139, 115, 91, 69, 57, 41, 29.

EXAMPLE 3

(S)-(+)-4-(5-Epoxypentyloxy)-2"-fluoro-4"-(2-methylbutyl)-1,1':4',1"-terphenyl

Preparation of (S)-(+)-4-(5-Epoxypentyloxy)-2"-fluoro-4"-(2-methylbutyl)-1,1':4',1"-terphenyl was performed according reaction scheme 4, STEP 2 using (S)-(+)-2'-fluoro-4"-(2-methylbutyl)4-(pent-5-enyloxy)-1,1':4',1"-terphenyl; 0.4 g (41% yield), 98.9% pure by HPCL. HTP= 4.902 μm$^{-1}$.

MS: m/z 419, 418(M+), 361, 335, 334, 303, 279, 277, 248, 233, 183, 139, 91, 86, 85, 57, 41, 29.

EXAMPLE 4

(S)-(+)-2-Fluoro-4"-(2-methylbutyl)4-(3-vinyloxypropoxy)-1,1':4',1"-terphenyl

Preparation of (S)-(+)-2-Fluoro-4"-(2-methylbutyl)-4(-3-vinyloxypropoxy)-1,1':4',1"-terphenyl was performed according reaction scheme 3, STEP 1 using (S)-(+)-2'-fluoro4-(3-hydroxypropoxy)-4"-(2-methylbutyl)-1,1':4',1"-terphenyl; 1.3 g (56% yield), 97.8% pure by HPCL.

EXAMPLE 5

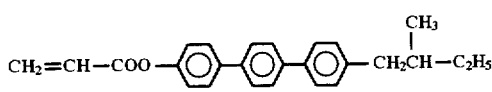

a) (S)-(+)4-Benzyloxy-4"-(2-methylbutyl)-1,1':4',1"-terphenyl

Preparation of (S)-(+)-4-benzyloxy-4"-(2-methylbutyl)-1,1':4',1"-terphenyl was performed according reaction scheme 1, STEP 1 using (S)-(+)-4-bromo-4'-(2-methylbutyl)biphenyl and 4-benzyl-oxyphenyl boronic acid; 12.0 g (60% yield). 99% pure by HPLC.

MS: m/z 307, 406(M+), 349, 317, 316, 259, 258, 231, 230, 215, 202, 165, 92, 91, 89, 65, 57, 41, 28.

b) (S)-(+)-4-Hydroxy-4"-(2-methylbutyl)-1,1':4',1"-terphenyl

Preparation of (S)-(+)4-hydroxy-4"-(2-methylbutyl)-1,1':4',1" terphenyl was performed according reaction scheme 1, STEP 2 using (S)-(+)4-benzyloxy"-(2-methylbutyl)-1,1':4',1"-terphenyl and 5% w/w palladium on charcoal as the heterogeneous catalyst; 7.5 g (84% yield). 97% pure by HPLC.

MS: m/z 318, 317, 316(M+?), 287, 272, 261, 260, 259, 257, 240, 239, 226, 215, 202, 189, 178, 166, 165, 152, 139, 129, 115, 107, 101, 89, 77, 65, 57, 55, 41, 29, 28.

c) (S)-(+)4-Acryloyloxy4"-(2-methylbutyl)-1,1':4',1"-terphenyl

Preparation of (S)-(+)-4-acryloyloxy4"-(2-methylbutyl)-1,1':4',1"-terphenyl was performed according reaction scheme 1, STEP 3 using (S)-(+)4-hydroxy-4"-(2-methylbutyl)-1,1':4',1"-terphenyl; 0.3 g (13% yield). 95% pure by HPLC. C 194 S 204.4 N*216.8 BP 217.8I. HTP=5.780 μm$^{-1}$.

MS: m/z 372, 371, 370(M+), 318, 317, 316, 313, 261, 260, 259, 258, 257, 231, 230, 215, 202, 189, 165, 139, 115, 57, 55, 41, 29, 28, 27.

EXAMPLE 6 a) (S)-(+)-4-(2-Methylbutyl)phenyl trifluoromethanesulphonate

Preparation of (S)-(+)-4-(2-methylbutyl)phenyl trifluoromethanesulphonate was performed according reaction scheme 2, STEP 1 using (S)-(+)-4-(2-methylbutyl)phenol; 46 g (92% yield). 93% pure by HPLC.

MS: m/z 296(M+).

b) (S)-(+)-4-Benyloxy-2'-fluoro-4"(2-methylbutyl)-1,1':4',1"-terphenyl

Preparation of (S)-(+)-4-benyloxy-2'-fluoro4"-(2-methylbutyl)-1,1':4',1"-terphenyl was performed according reaction scheme 2, STEP 2 using 4'-benzyloxy-2-fluoro-4-biphenylboronic acid and (S)-(+)-4-(2-methylbutyl)phenyl trifluoromethanesulphonate. The crude product was recrystallized from o-xylene (80 ml); 14.5 g (66% yield). 94% pure by HPLC.

MS: m/z 424(M+).

c) (S)-(+)-2'-Fluoro-4"-(2-methylbutyl)-1,1':4',1"-terphenyl

Preparation of (S)-(+)-2'-fluoro-4"-(2-methylbutyl)-1,1':4', 1"-terphenyl was performed according reaction scheme 2, STEP 3 using (S)-(+)-4'-benzyloxy-2'-fluoro-4"-(2-methylbutyl)-1,1':4',1"-terphenyl and 5% w/w palladium on charcoal as the heterogeneous catalyst; 11 g (98% yield). 94% pure by HPLC.

MS: m/z 334(M+).

d) (3)-(+)4-Acryloyloxy-2'-fluoro4"-(2-methylbutyl)-1,1':4', 1"-terphenyl

Preparation of (3)—(+)-4-acryloyloxy-2'-fluoro4"-(2-methylbutyl)1,1':4',1"-terphenyl was performed according reaction scheme 2, STEP 6 using (S)-(+)-2-fluoro-4-hydroxy-4"-(2-methylbutyl)-1,1':4',1"-terphenyl; 2.0 g (70% yield). 99.1% pure by HPLC. C 61.5 N*167.2 BP 167.8 I. HTP=5.051 μm$^{-1}$.

MS: m/z 390, 389, 368(M+), 336, 335, 334, 331, 290, 279, 278, 277, 261, 249, 233, 220, 207, 183, 157, 133, 115, 91, 65, 57, 55, 41, 29, 27.

EXAMPLE 7

A mixture is formulated consisting of

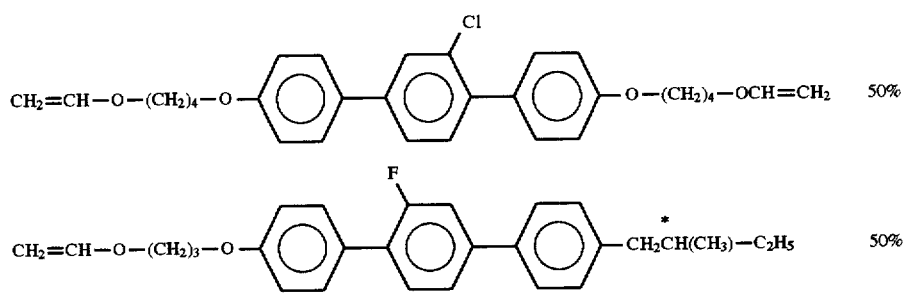

$\lambda_{max}$ =540 nm

Supercools to toom temperature and crystallizes slowly over 3 days.

EXAMPLE 8

A mixture is formulated consisting of

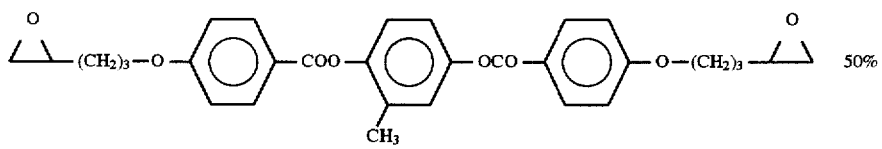
50%

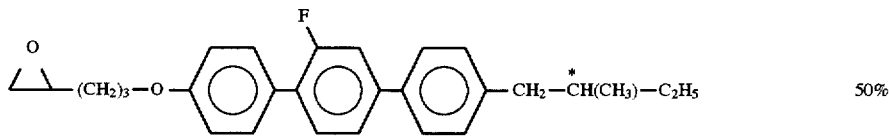
50%

K42 N*130I $\lambda_{max}$=560 nm

Supercools to room temperature and crystallizes overnight.

EXAMPLE 9

Mixtures are formulated consisting of

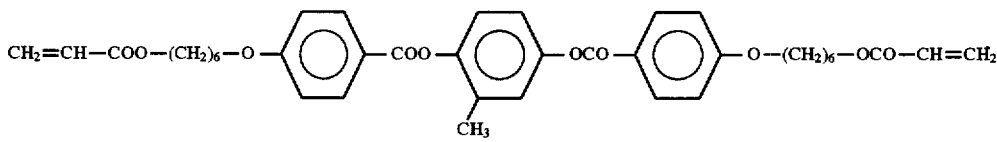

50% by weight and a chiral monoacrylate 50% of the following structure:

9A:

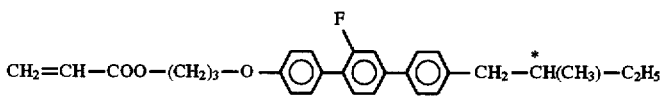

9B:

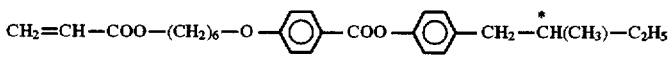

9C:

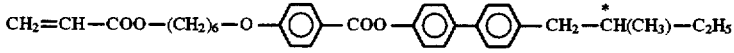

The mixtures show following phase transition temperatures:

9A: K61 N*104I
9B: K64 (N* 59) I
9C: K60 N*118I

1% of the commercially available photoinitiator is added (coded Irgacure IR 651) and the mixture is photopolymerized to yield a cholesteric film. The resulting film shows the following properties.

| Mixture | curing temperature [°C.] | λmax [nm] | Δλ [nm] |
|---|---|---|---|
| 9A | 85 | 515 | 95 |
| 9B | 40 | 515 | 65 |
| 9C | 85 | 645 | 75 |

The inventive chiral terphenyl produces clearly broader bandwidths (Δλ) than the conventional chiral compounds.

EXAMPLE 10

Mixtures are formulated consisting of

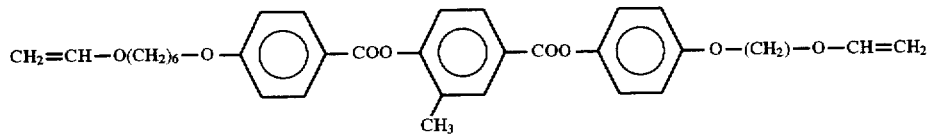

50% by weight, and a chiral monovinylether 50% of the following structure:

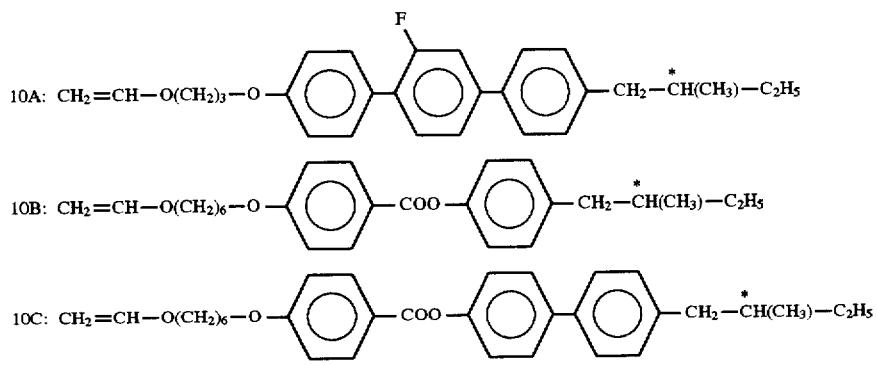

The mixtures show the following phase transistions:
10A: K34N*(?)I
10B: K50N*118I
10C: K65N*120I 1% of the commercially available photoinitiator IR 651 and 1% of the commercially available photoinitiator Degacure K 185 are added, the mixture is photopolymerized to yield a cholesteric film.

This film shows the following properties:

| Mixture | curing temperature [°C.] | λmax [nm] | Δλ [nm] |
|---|---|---|---|
| 10A | 85 | 530 | 115 |
| 10B | 40 | 515 | 65 |
| 10C | 85 | 720 | 115 |

EXAMPLE 11

Mixtxures are formulated consisting of

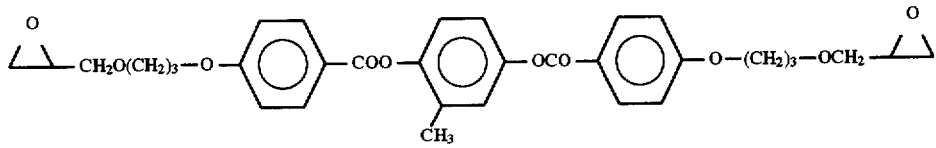

50 % bei weight, and a chiral monoepoxy compound of the following structure:

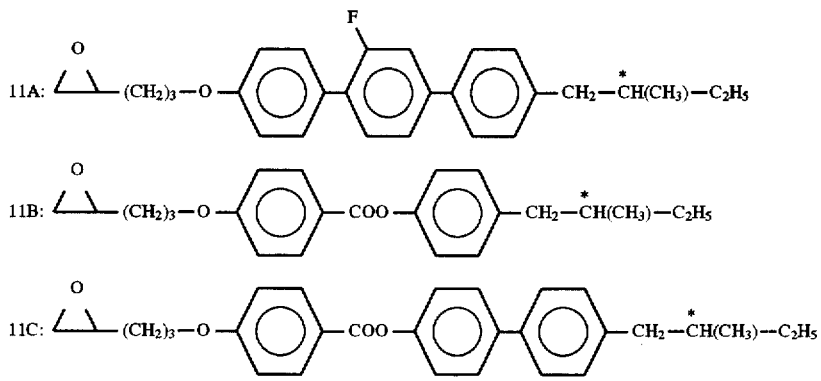

The mixtures show the following phase transistion temperatures:
11A: K33N*107I
11B: K35N*(?)I
11C: K53N*127I 1% of IR 651 and 1% of K184 are added and the mixture is photopolymerized to yield a cholesteric film.
This film shows the following properties:

| Mixture | curing temperature [°C.] | λmax [nm] | Δλ [nm] |
|---|---|---|---|
| 11A | 85 | 500 | 140 |
| 11B | 40 | 520 | 75 |
| 11C | 85 | 650 | 90 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:
1. Monofunctional reactive terphenyl of formula I

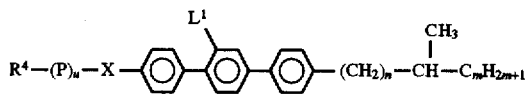

in which
R$^4$ is CH$_2$=CW—COO—,

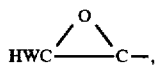

HWN—, CH$_2$=CH—, CH$_2$=CH—O— or HS—CH$_2$—(CH$_2$)$_m$—COO— with W being H, Cl or alkyl with 1–5 C atoms and m being 1–7, P is alkylene with up to 12 C atoms, it being also possible for one or more non adjacent CH$_2$ groups to be replaced by —O—,
L$^1$ is F,
X is —O—, —S—, —COO—, —OCO— or a single bond,
u is 0 or 1,
n is an integer 1 to 8, and
m is an integer 2 to 8.

2. Monofunctional reactive terphenyl of formula I in which
n is 1, and
m is 2.

3. Copolymerizable precursor material comprising at least one polymerizable terphenyl of formula I of claim 1 and at least one bifunctional reactive achiral compound of formula II $$R^4\text{—}(P)_u\text{—}MG^1\text{—}(P)_uR^4 \qquad \text{II}$$

wherein R$^4$, P and u have the meaning given, and
MG$^1$ is a mesogenic group.

4. Copolymerizable material according to claim 3 comprising at least one bifunctional reactive achiral compound of formula II and at least one reactive chiral terphenyl of formula I in which
R$^4$ is an acrylate radical of formula

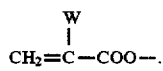

5. Copolymerizable material according to claim 3, comprising at least one compound of formula II and at least one compound of formula I in which R$^4$ is a vinylether radical of formula CH$_2$=CH—O—.

6. Copolymerizable material according to claim 3 in which MG$^1$ is selected from

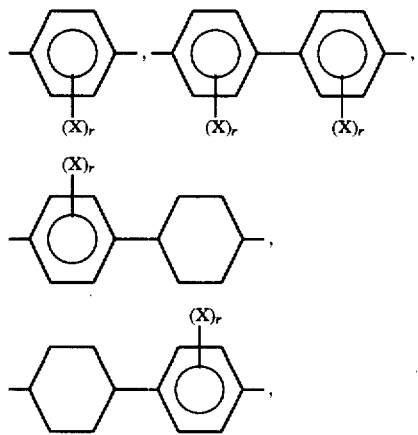

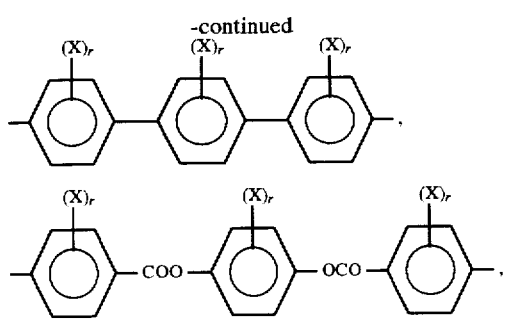

with X being CN or F and r being 0, 1 or 2.

7. A chiral smectic or nematic polymer film obtainable by in-situ (co)polymerization of a polymerizable terphenyl of formula I or a copolymerizable material according to claim 3.

8. Polymer film according to claim 7 being capable of reflecting light of visible wavelengths with a broad band of the reflected wavelength band.

9. A method of using a polymer film according to claim 8 which comprises employing said polymer film as a broadband polarizer.

* * * * *